United States Patent
Dobashi

(10) Patent No.: US 7,850,768 B2
(45) Date of Patent: Dec. 14, 2010

(54) AIR FILTERING APPARATUS HAVING SCALE REMOVAL DETECTING MECHANISM

(75) Inventor: Mitsuhiro Dobashi, Saitama (JP)

(73) Assignee: Sanyo Electric Co., Ltd., Moriguchi-shi (JP)

(*) Notice: Subject to any disclaimer, the term of this patent is extended or adjusted under 35 U.S.C. 154(b) by 380 days.

(21) Appl. No.: 11/860,966

(22) Filed: Sep. 25, 2007

(65) Prior Publication Data

US 2008/0072757 A1    Mar. 27, 2008

(30) Foreign Application Priority Data

Sep. 26, 2006    (JP) ............................. 2006-261304

(51) Int. Cl.
*B01D 47/00* (2006.01)
(52) U.S. Cl. ............................. 96/234; 96/240; 96/244; 96/265
(58) Field of Classification Search ................ 96/234, 96/240, 243, 244, 265
See application file for complete search history.

(56) References Cited

U.S. PATENT DOCUMENTS

| | | | |
|---|---|---|---|
| 3,476,673 A | 11/1969 | Stiles | |
| 4,663,091 A | 5/1987 | Seo et al. | |
| 5,916,490 A | 6/1999 | Cho | |
| 2001/0004962 A1* | 6/2001 | Hirota et al. | 204/228.1 |
| 2003/0085301 A1* | 5/2003 | Ganoza et al. | 239/266 |
| 2005/0072308 A1* | 4/2005 | Aoyagi | 96/235 |

FOREIGN PATENT DOCUMENTS

| | | |
|---|---|---|
| JP | 06165984 | 6/1994 |
| JP | 2002-181358 A | 6/2002 |
| JP | 2003250876 | 9/2003 |

* cited by examiner

*Primary Examiner*—Duane Smith
*Assistant Examiner*—Tiffany N Palmer
(74) *Attorney, Agent, or Firm*—Westerman, Hattori, Daniels & Adrian, LLP

(57) ABSTRACT

An air filtering apparatus for electrolyzing water in an electrolytic bath by applying a voltage between electrodes in the electrolytic bath, supplying the generated electrolytic water to a gas-liquid contact member and blowing air to the gas-liquid contact member to filter the air, including a scale removing unit for inverting the polarities of the electrodes to remove scale deposited on the electrodes, and a judging unit for judging on the basis of a current value flowing between the electrodes whether the scale is removed from the surface of the electrode.

5 Claims, 9 Drawing Sheets

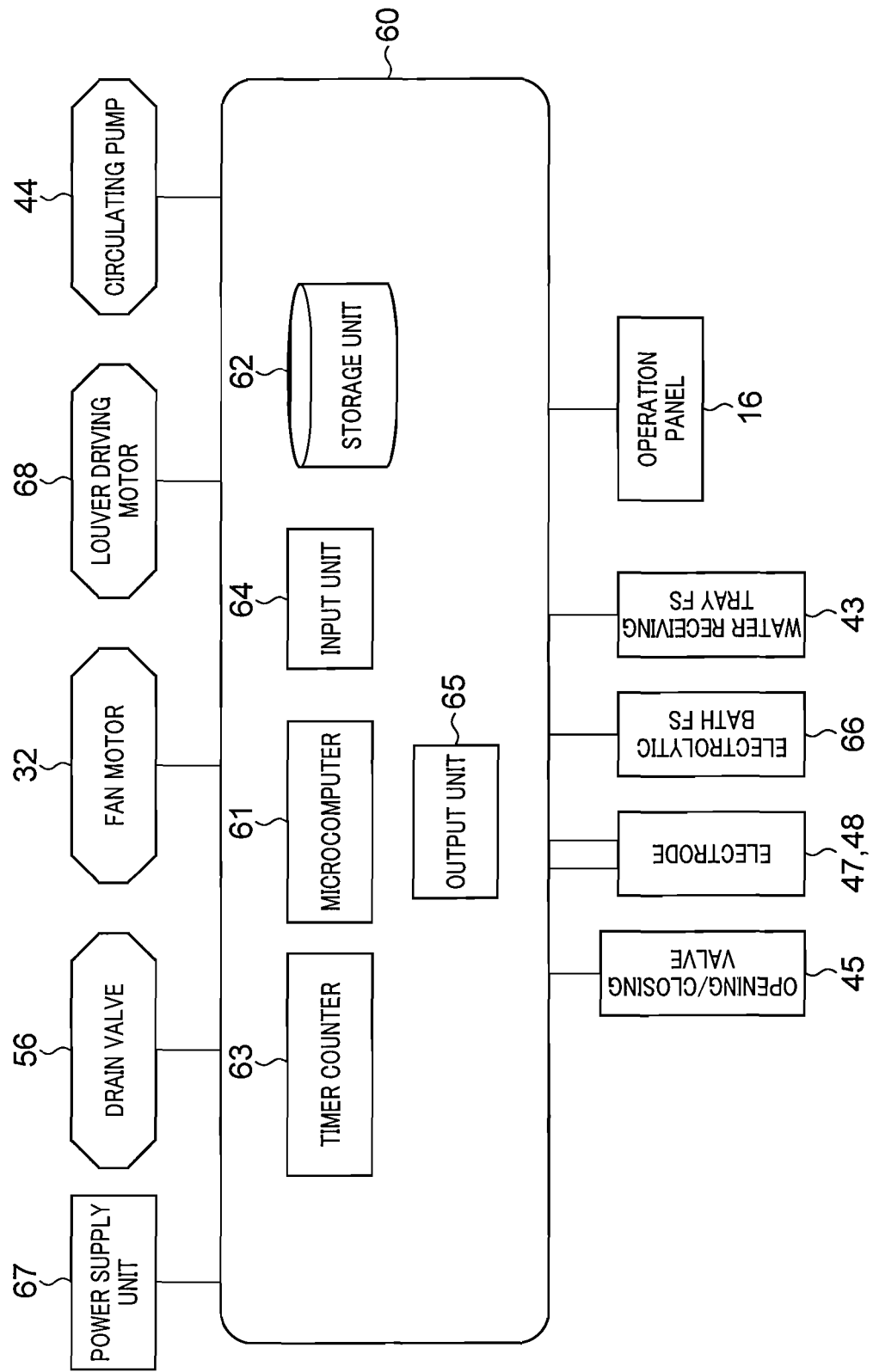

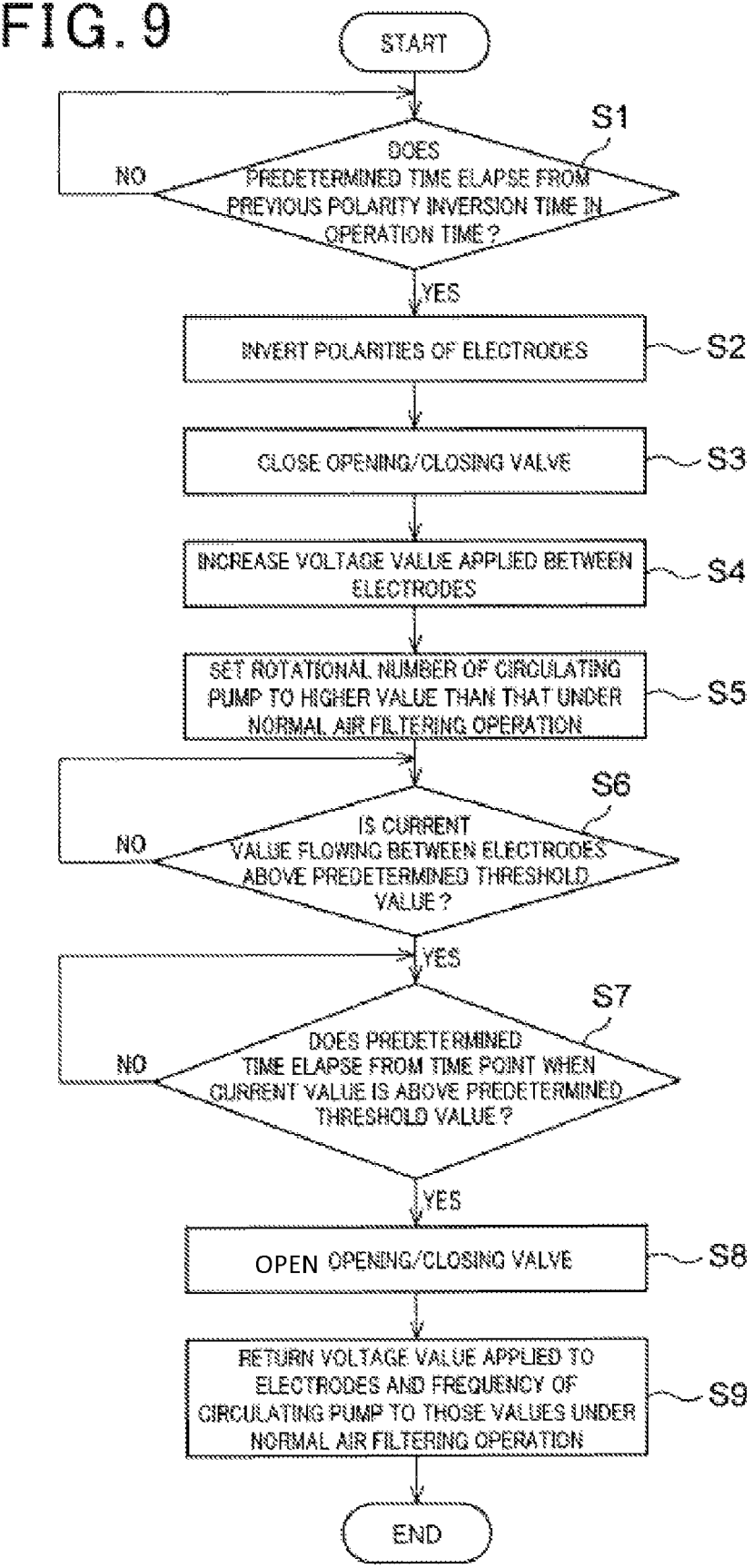

AIR FILTERING APPARATUS HAVING SCALE REMOVAL DETECTING MECHANISM

INCORPORATION BY REFERENCE

The present application claims priority under 35 U.S.C. §119 to Japanese Patent Application No. 2006-261304 filed on Sep. 26, 2006. The content of the application is incorporated herein by reference in its entirety.

BACKGROUND OF THE INVENTION

1. Field of the Invention

The present invention relates to an air filtering apparatus that can remove microorganisms floating in the air such as bacteria, virus, fungus, etc. (hereinafter merely referred to as "virus, etc."), and more particularly to an air filtering apparatus having a scale removal detecting mechanism.

2. Description of the Related Art

There has been proposed a filtering apparatus in which tap water is electrolyzed to generate electrolytic water containing active oxygen species such as hypochlorous acid or the like, and virus, etc. floating in the air are removed by using this electrolytic water (for example, see JP-A-2002-181358). According to this filtering apparatus, electrolytic water is supplied to a humidifying element formed of non-woven cloth or the like, and virus, etc. in the air are brought into contact with the electrolytic water in the humidifying element to inactivate the virus, etc., thereby filtering the air.

However, in the above air filtering apparatus, scale is generated and deposited on electrodes for electrolysis due to metal ions, calcium ions or magnesium ions contained in water used to generate electrolytic water, so that electrolysis performance and durability are reduced when the air filtering apparatus is operated for a long time and thus the air filtering performance itself is lowered. Therefore, there is a problem that the labor for maintenance of the electrodes is increased.

SUMMARY OF THE INVENTION

An object of the present invention is to provide an air filtering apparatus that can maintain electrolysis performance and durability even under a long-term operation and thus maintain air filtering performance, and also reduce the labor for maintenance of electrodes.

In order to attain the above object, according to the present invention, an air filtering apparatus for electrolyzing water in an electrolytic bath by applying a voltage between electrodes in the electrolytic bath, supplying the generated electrolytic water to a gas-liquid contact member and blowing air to the gas-liquid contact member to filter the air comprises a scale removing unit for inverting the polarities of the electrodes to remove scale deposited on the electrodes, and a judging unit for judging on the basis of a current value flowing between the electrodes whether the scale is removed from the surface of the electrode.

In this case, when the current value increases to a predetermined threshold value or more, the judging unit may judge that the scale is removed from the electrode surface. Furthermore, the air filtering apparatus may be further equipped with a bypass passage through which electrolytic water flowing out from the electrolytic bath bypasses the gas-liquid contact member, and a bypass valve for prohibiting the electrolytic water containing the scale from being supplied to the gas-liquid contact member and guiding the electrolytic water to the bypass passage.

In this case, when it is judged that the scale has been removed from the electrode surface, the bypass valve may be controlled to allow supply of the electrolytic water to the gas-liquid contact member. Furthermore, the bypass passage may be equipped with a filter unit for collecting the scale. The filter unit may be disposed in a water receiving tray for receiving water passing through the gas-liquid contact member.

According to the present invention, the scale deposited on the electrode is removed by inverting the polarities of the electrodes, and thus the labor for maintenance of the electrodes can be reduced, and the maintenance frequency can be reduced. Furthermore, it is judged on the basis of the current value flowing between the electrodes whether the scale has been removed from the surfaces of the electrodes, and thus the operation can be shifted to the air filtering operation immediately after the scale is removed, for example. Therefore, the air filtering operation can be efficiently performed.

BRIEF DESCRIPTION OF THE DRAWINGS

FIG. 8 is a functional block diagram showing the construction of a control system for the air filtering apparatus; and FIG. 9 is a flowchart showing the operation of discharging scale exfoliated from the electrodes to a filter unit.

DETAILED DESCRIPTION OF THE PREFERRED EMBODIMENTS

Preferred embodiments according to the present invention will be described hereunder with reference to the accompanying drawings.

Figure 1:
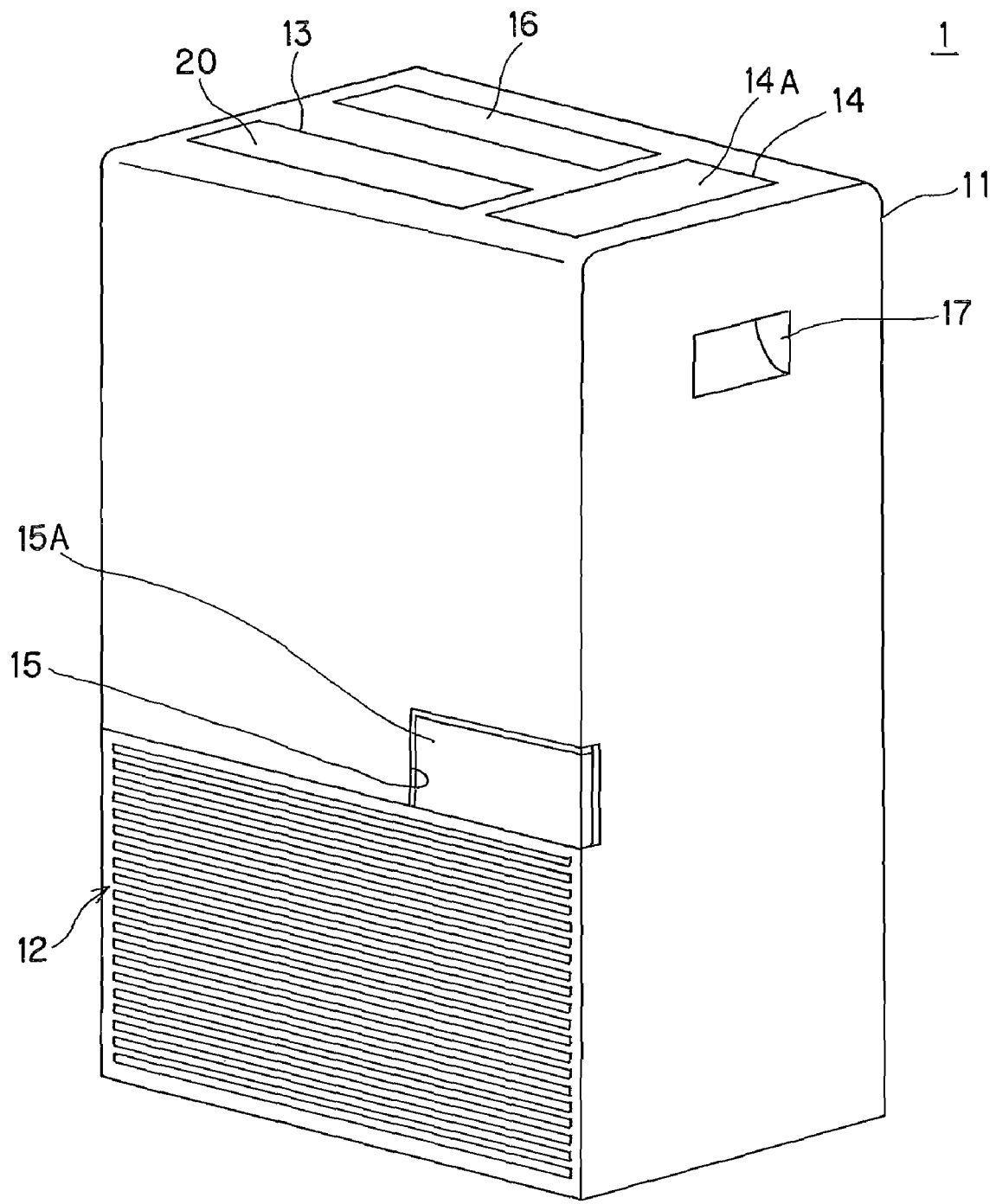
FIG. 1 is a perspective view showing the outlook of an air filtering apparatus according to an embodiment of the present invention.

FIG. 1 is a perspective view showing the outlook of an air filtering apparatus 1 according to an embodiment to which the present invention is applied.

As shown in FIG. 1, the air filtering apparatus 1 has a vertically long box-shaped housing 11, and it is set on the floor, for example. An suction grille 12 is provided to the lower portion of the front face of the housing 11, and an air blow-out port 13 as an exhaust port is provided to the top face of the housing 11. A louver 20 for changing the air blowing direction of air is provided to the air blow-out port 13.

The air filtering apparatus 1 sucks and filters air through the suction grille 12 from a room where the air filtering apparatus is set, and blowing out the filtered air from the air blow-out port 13 into the room, thereby cleaning the indoor air.

The top face of the housing 11 is equipped with an operation panel 16 for carrying out various kinds of operations of the air filtering apparatus 1, and a water supply tank take-out port 14 through which a water supply tank 41 (FIG. 2) described later is inserted or taken out. An openable and closable lid 14A is secured to the water supply tank take-out port 14. Furthermore, the front face of the housing 11 is equipped with a drain receiver take-out port 15 through which a drain receiver 57 (FIG. 2) described later is inserted and taken out, and an openable and closable lid 15A is secured to the drain receiver take-out port 15.

A grip portion 17 is formed at each of the upper portions of both the side faces of the housing 11. These grip portions 17 are recess portions (handholds) on which user's hands put when the housing 11 is lifted by hands. Accordingly, a user can lift and move the air filtering apparatus by himself/herself while carrying the air filtering apparatus.

Next, the internal construction of the air filtering apparatus 1 according to this embodiment will be described with reference to FIGS. 2 to 6

Figure 2:
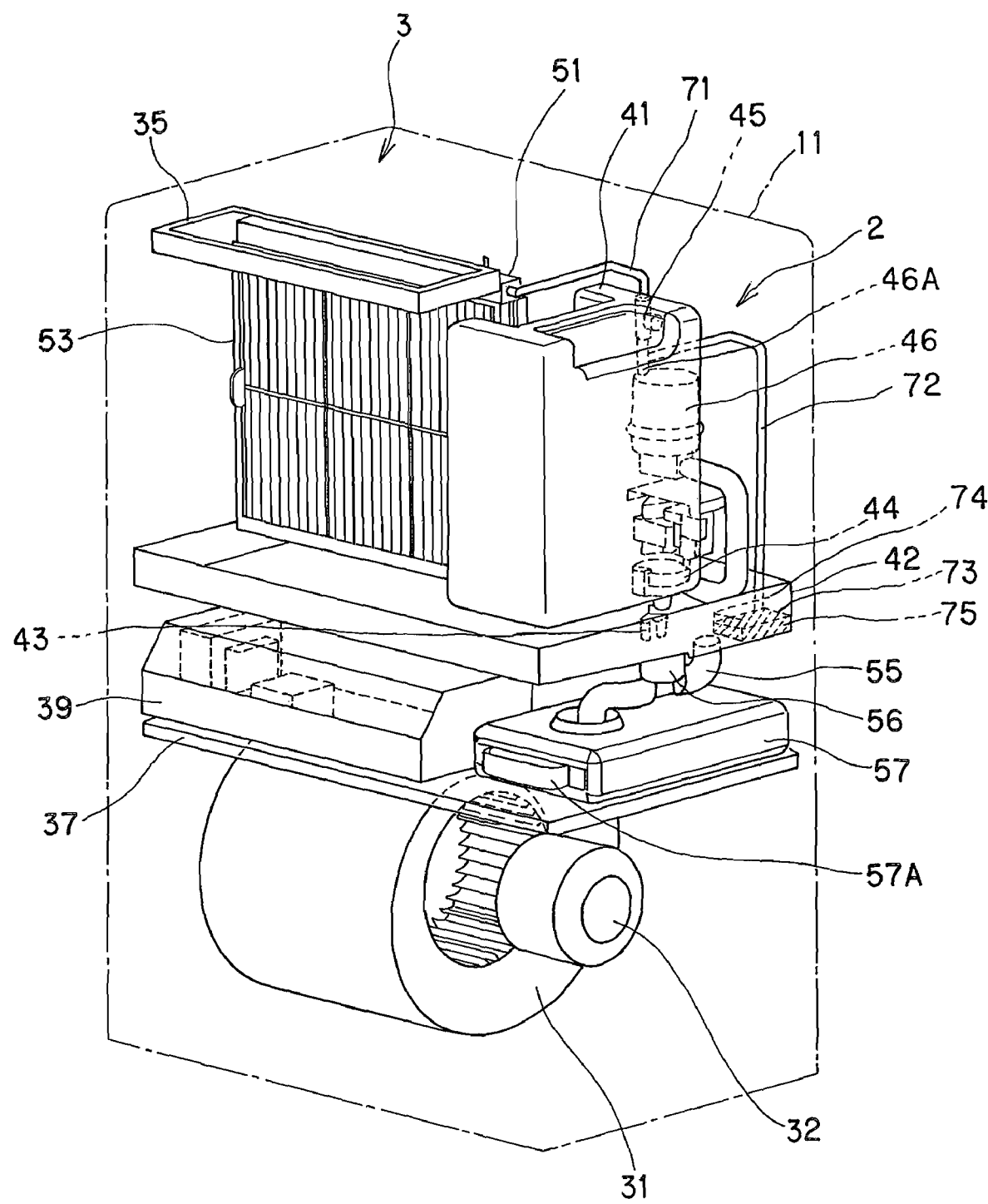
FIG. 2 is a perspective view showing the internal construction of the air filtering apparatus.
Figure 3:
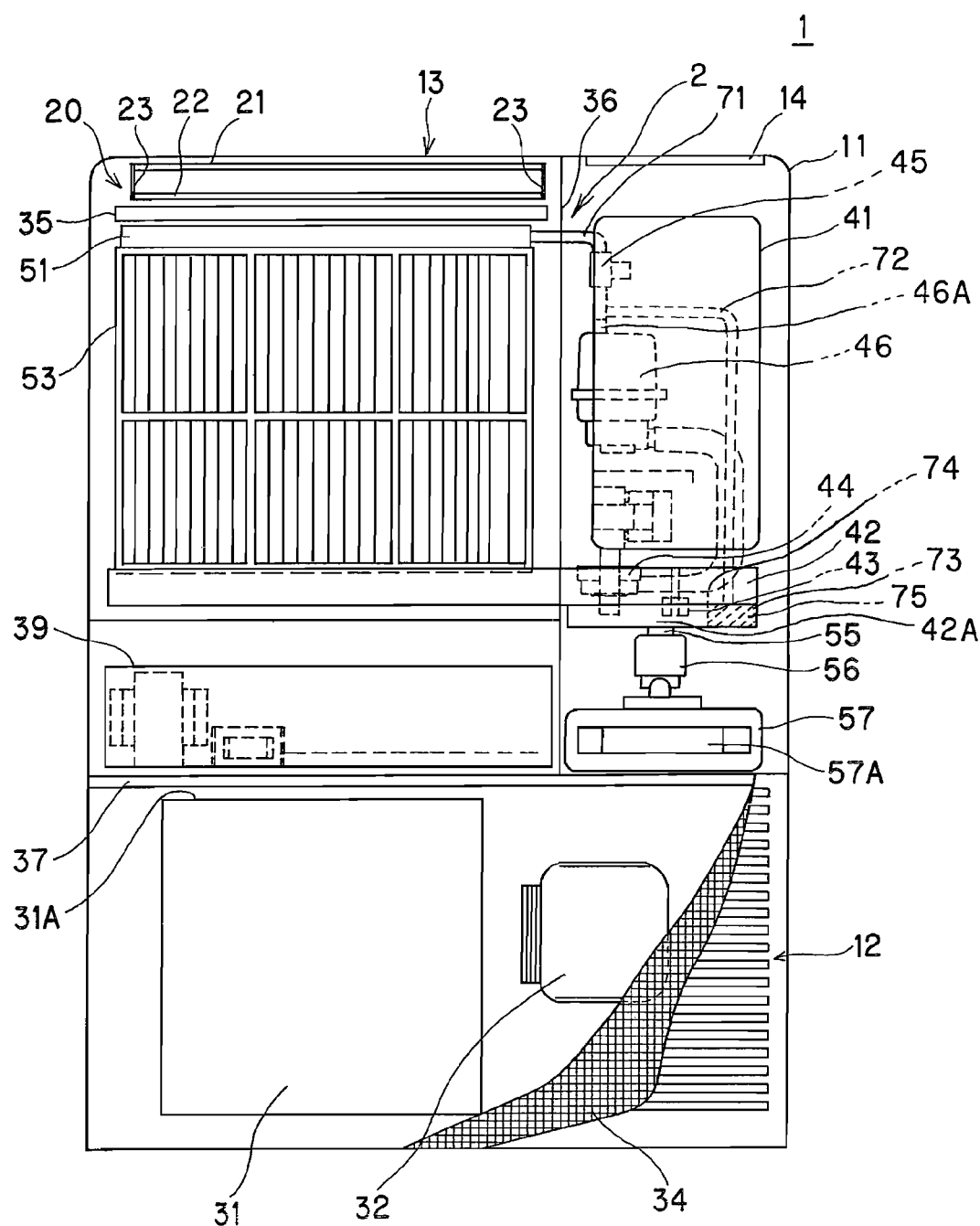
FIG. 3 is a partially fracture front view showing the internal construction of the air filtering apparatus.
Figure 4:
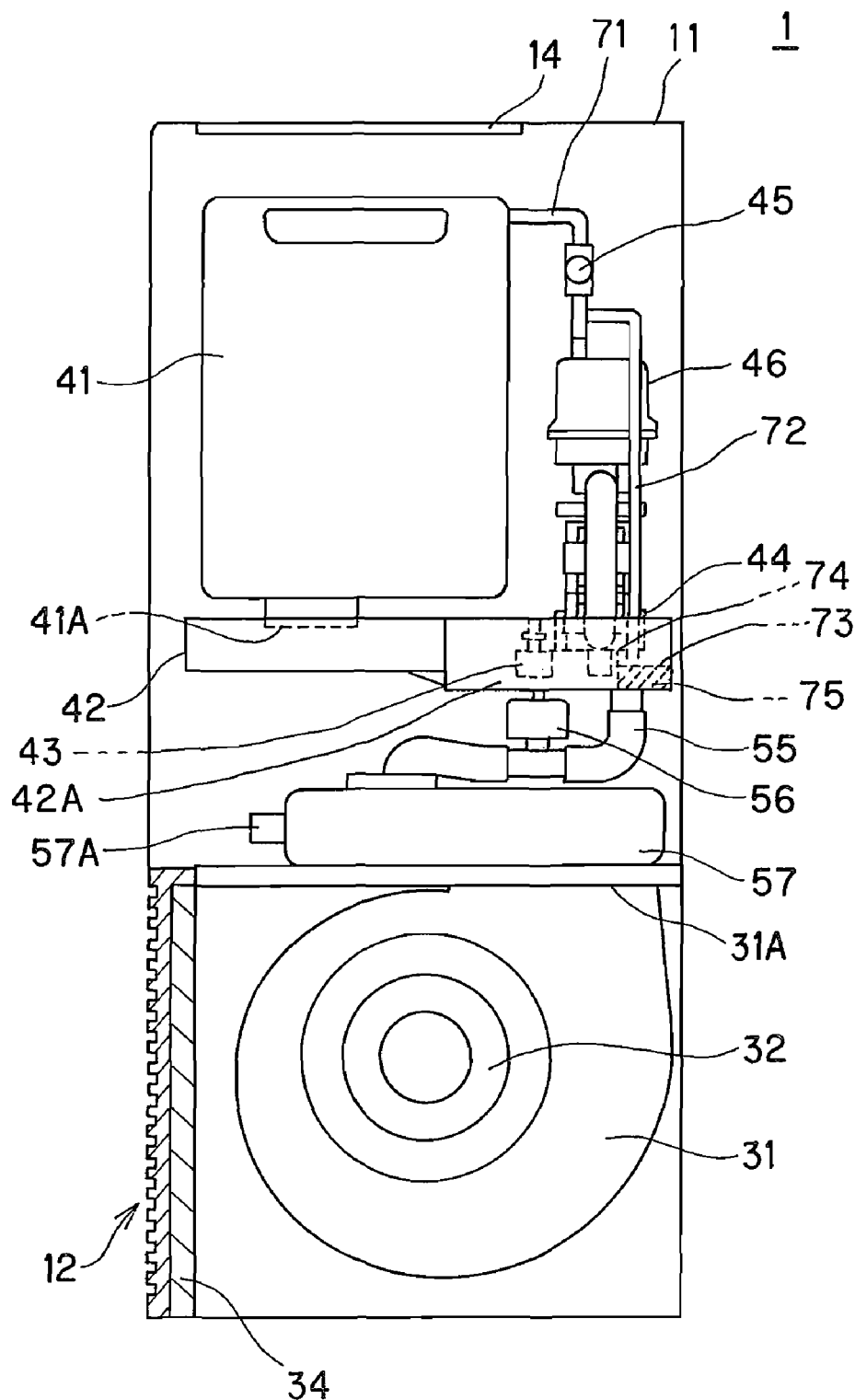
FIG. 4 is a left-side sectional view showing the internal construction of the air filtering apparatus.
Figure 5:
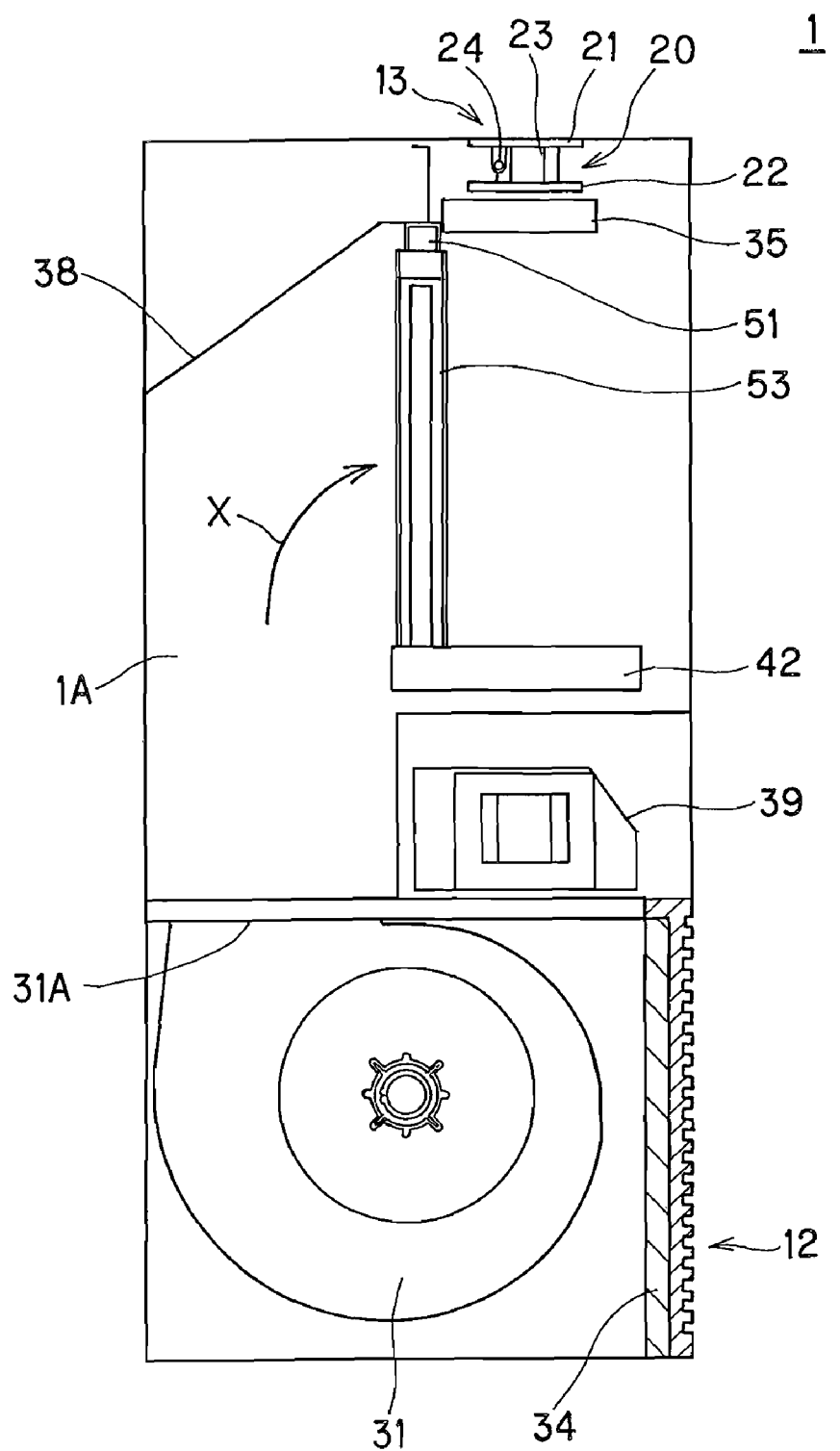
FIG. 5 is a right-side sectional view showing the internal construction of the air filtering apparatus.
Figure 6:
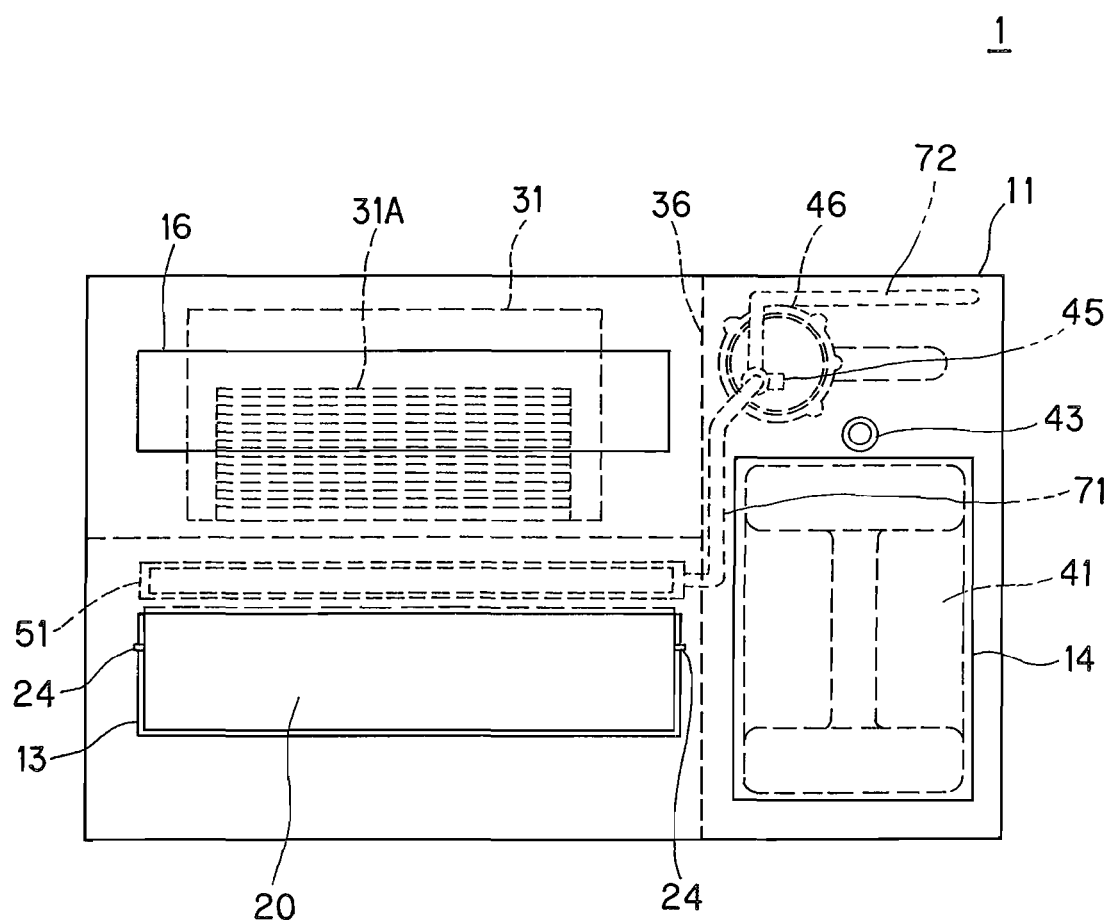
FIG. 6 is a top view showing the internal construction of the air filtering apparatus.

FIG. 2 is a perspective view showing the internal construction of the air filtering apparatus 1. In FIG. 2, the outline of the housing 11 is illustrated by virtual lines for reference. FIG. 3 is a partially fracture front view showing the construction of the air filtering apparatus 1, FIG. 4 is a left-side sectional view, FIG. 5 is a right-side sectional view and FIG. 6 is a top view.

The inside of the housing 11 is partitioned vertically into upper and lower chambers by a support plate 37. An air blowing fan 31 and a fan motor 32 are accommodated in the lower chamber. The air blowing fan 31 is driven by the fan motor 32 to suck indoor air through the suction grille 12 and blow out the air from the air flow-out port 31A. The air flow-out port 31A of the air blowing fan 31 is at the back side portion of the housing 11 so as to be placed face up, and an opening is formed in the support plate 37 so as to be overlapped with the air flow-out port 31A. The opening of the support plate 37 intercommunicates with the space 1A extending vertically at the back side of the housing 11. An air guide plate 38 which is tilted to the front side of the housing 11 is disposed at the upper portion of the space 1a as shown in FIG. 5, and the front end of the air guide plate 38 is brought into contact with the upper end of a water spray box 51 described later.

Therefore, air blown out from the air flow-out port 31A of the air blowing fan 31 passes through the space 1A as indicated by an arrow X in FIG. 5, and blows to the back side of a gas-liquid contact member 53 described later.

Furthermore, a pre-filter 34 is disposed in the housing 11 so as to be overlaid on the back side of the suction grille 12. The pre-filter 34 is a filter for collecting materials (foreign materials such as dust, grass pollen, etc.) of 10 μm or more in particle diameter, for examples. Foreign materials such as dust, grass pollen, etc. are removed by the pre-filter 34, and air from which these foreign materials are removed is sucked by the air blowing fan 31.

An electrical component box 39 and an electrolytic water circulating unit 2 are disposed on the support plate 37. In the electrical component box 39 are accommodated various kinds of electrical components such as a control board (not shown) on which various kinds of devices constituting a controller 60 described later are mounted, a power supply circuit for supplying a power supply voltage to the fan motor 32, etc.

The electrolytic water circulating unit 2 comprises a water receiving tray 42, a water receiving tray float switch 43, a circulating pump 44, an electrolytic bath 46, a water spray box 51 and the gas-liquid contact member 53. The water receiving tray 42 is located above the electrical component box 39, and receives water dropped form the gas-liquid contact member 53. Accordingly, the water receiving tray 42 has a depth to stock a predetermined amount of water. One end portion of the water receiving tray 42 is designed to have a bottom deeper than the other portion, and it serves as a stock portion 42A. The water receiving tray float switch 43 for detecting the water level is disposed at the stock portion 42A. The water receiving tray float switch 43 is turned on when the water level of the stock portion 42A is lower than a predetermined water level.

The water supply tank 41 is disposed above the stock portion 42A, and it is designed so as to supply water from the water supply tank 41 to the stock portion 42A. In detail, a float valve (not shown) is provided to a water supply port 41A formed at the lower end of the water supply tank 41. When the water level of the stock portion 42A is lower than the water supply port 41A, the float valve is opened, so that a required amount of water is supplied form the water supply tank 41 so that the water level of the stock portion 42A is kept constant.

The circulating pump 44 is disposed above the stock portion 42A. The circulating pump 44 operates so that the circulation amount is changeable by changing the rotational number thereof according to the control of the controller 60 (FIG. 8), and pumps up water stocked in the stock portion 42A to feed the water to the electrolytic bath 46. This electrolytic bath 46 contains plural electrodes described later, and a voltage supplied from the controller 60 (FIG. 8) is applied between the electrodes to electrolyze water, thereby generating electrolytic water containing active oxygen species.

A discharge port 46A for draining electrolytic water generated in the electrolytic bath 46 is formed on the top surface of the electrolytic bath 46, and a water feed pipe 71 is connected to the discharge port 46A through an opening/closing valve (bypass valve) 45, and the water feed pipe 71 is connected to the water spray box 51. Accordingly, electrolytic water generated in the electrolytic bath 46 is pushed out from the electrolytic bath 46 by water discharged by the circulating pump 44, and supplied through the water feed pipe 71 to the water spray box 51.

Furthermore, a bypass pipe (bypass passage) 72 branched from the water feed pipe 71 is connected between the discharge port 46A of the electrolytic bath 46 and the opening/closing valve 45. By closing the opening/closing valve 45, the bypass pipe 72 returns the electrolytic water generated in the electrolytic bath 46 to the water receiving tray 42 while the electrolytic water bypasses the gas-liquid contact member 53. This opening/closing valve 45 is opened/closed under the control of the controller 60 (FIG. 8).

In this embodiment, a filter unit 73 for filtering the electrolytic water returned through the bypass pipe 72 is formed at the stock portion 42A of the water receiving tray 42. The filter unit 73 comprises a dam 74 formed in the stock portion 42A and a filter member 75 disposed in the recess portion surrounded by the dam 74, and the bypass pipe 72 is disposed above the filter unit 73. The dam 74 of the filter unit 73 is formed to be lower than the peripheral wall of the water receiving tray 42 and higher than the depth of the stock portion 42A. Accordingly, water stocked in the filter unit 73 flows over the dam 74 and flows into the stock portion 42A. Furthermore, the filter member 75 is a filter formed of nonwoven cloth or glass fiber, and solid materials (for example, scale) flowing into the filter member 75 together with water get stuck on the surface of the filter member 75, so that the solid materials are collected.

When the opening/closing valve 45 is closed during the operation of the circulating pump 44, electrolytic water discharged from the electrolytic bath 46 is returned through the bypass pipe 72, and flows into the filter unit 73. In this case, the solid materials contained in the electrolytic water are collected by the filter member 75, and the electrolytic water from which the solid materials are removed flows over the dam 74 into the water receiving tray 42 and is fed to the electrolytic bath 46 again by the circulating pump 44. Accordingly, scale in the electrolytic water is collected by the filter unit 73, and thus the scale is prevented from flowing into the gas-liquid contact member 53, whereby the gas-liquid contact member 53 can be prevented from being clogged.

In this construction, the bypass pipe 72 is provided with no valve for stopping flow of water into the bypass pipe 72. Therefore, even under the air filtering operation (normal operation) in which the opening/closing valve 45 is opened to supply electrolytic water to the gas-liquid contact member 53, a part of electrolytic water flowing out from the electrolytic bath 46 is returned to the filter unit 73 of the water receiving tray 42 through the bypass pipe 72. According to this construction, a part of the electrolytic water is filtered by the filter unit 73 at all times, and thus the solid materials in the electrolytic water can be reduced, so that the clogging of the gas-liquid contact member 53 can be prevented. Furthermore, the filter unit 73 is formed in the water receiving tray under the state that the upper portion thereof is opened. Therefore the exchange timing of the filter unit 75 can be simply judged through visual check. Still furthermore, when the filter member 75 is exchanged, the filter member 75 disposed in the filter unit 73 may be detached and exchanged by hands. Therefore, no tool is necessary for the exchange work and the maintenance can be simply performed.

The water spray box 51 is a tubular member assembled to the upper portion of the gas-liquid contact member 53. Plural water spray holes (not shown) are formed at the lower surface of the water spray box 51, and electrolytic water is dropped form the water spray holes to the gas-liquid contact member 53. The gas-liquid contact member 53 is a substantially planar member infiltrated with electrolytic water dropped from the water spray box 51, and it is disposed above the water receiving tray 52 together with the water spray box 51. As shown in detail in FIG. 5, the gas-liquid contact member 53 is substantially vertically erected, and the lower end thereof intrudes into the water receiving tray 42. Furthermore, the water spray box 51 assembled to the upper portion of the gas-liquid contact member 53 is brought into contact with the tip of the air guide plate 38. Therefore, the air passed through the space 1A by the air blowing fan 31 is guided to the gas-liquid contact member 53 side by the air guide plate 38, and passes through the gas-liquid contact member 53.

The gas-liquid contact member 53 is a filter member having a honeycomb structure. In details, the gas-liquid contact member 53 has the structure that an element portion which is brought into contact with gas is supported by a frame. The element portion is constructed by laminating corrugated-plate type corrugated members and flat-plate type planar members, and many openings having substantially triangular shapes are formed among these corrugated members and the planar members. Accordingly, the gas-liquid contact member 532 has the structure in which a large gas contact area can be secured when gas is passed through the element portion, electrolytic water can be dropped and also clogging occurs hardly.

Furthermore, a water distributing sheet (not shown) is provided to the gas-liquid contact member 53 in order to efficiently disperse electrolytic water dropped from the water spray box 51 into the element portion. The water distributing sheet is a sheet (woven fabric, non-woven cloth or the like) formed of textile material having liquid permeability, and one or plural water distributing sheets are provided along the cross-section taken along the thickness direction of the gas-liquid contact member 53.

Furthermore, the gas-liquid contact member 53 and the water supply tank 41 are insulated from each other by a partition plate 36. The partition plate 36 blocks off the space 1A and the side of the gas-liquid contact member 53, and makes air smoothly pass through the gas-contact member 53.

Here, the respective parts of the gas-liquid contact member 53 (containing the frame, the element portion and the water distributing sheet) are formed of materials which are little deteriorated by electrolytic water, such as polyolefin-based resin (polyethylene resin, polypropylene resin or the like), PET (polyethylene terephthalate) resin, vinyl chloride resin, fluorocarbon resin (PTFE, PFA, ETFE or the like), ceramic material or the like. In this embodiment, PET resin is assumed to be used.

Furthermore, the respective parts of the gas-liquid contact member 53 is subjected to a hydrophilic treatment to enhance the affinity to electrolytic water. Accordingly, water retentivity (wettability) of electrolytic water of the gas-liquid contact member 53 is kept, and the contact between active oxygen species (active oxygen materials) described later and indoor air can be kept for a long time. Furthermore, electrolytic water having a mildew proof action is dropped to the gas-liquid contact member 53, so that breeding of fungus, etc. can be avoided without taking any mildew proof action to the gas-liquid contact member 53.

Air passing through the gas-liquid contact member 53 is exhausted through an air blow-out filter 35 disposed below the air blow-out port 13. The air blow-out filter 35 is a filter for preventing invasion of foreign materials from the air blow-out port 13 into the housing 11. The air blow-out port filter 35 has a net, woven fabric, non-woven cloth or the like (not shown), and these materials are formed of synthetic resin, and preferably formed of the material constituting the gas-liquid contact member 53. The air blow-out filter 35 is preferably of moderately loose texture so that the air flowing resistance of air passing through the gas-liquid contact member 53 is not remarkably increased.

As described above, the louver 20 is disposed at the air blow-out port 13, and it is constructed by an upper plate 21 having a size at which the air blow-out port 13 can be closed, a lower plate 22 disposed in parallel to the upper plate 21 at the lower side of the upper plate 21, and joint portions 23 for joining the upper plate 21 and the lower plate 22. The joint portions 23 are plate-shaped members provided to the right and left end portions of each of the upper plate 21 and the lower plate 22, and a pin 24 is erected from each of the joint portions 23. These two pins 24 are projected from both the side ends of the louver 20 to the housing 11 side, and fitted to receivers (not shown) provided at the sides of the air blow-out port 13 to support the louver 20.

The two pins 24 are freely rotatably supported at the receivers, and joined to a louver driving motor 68 (see FIG. 8). The pins 24 are driven by the louver driving motor 68 and the louver 20 is turned in connection with the driving of the pins 24.

Under the state that the louver 20 is substantially in parallel to the upper face of the housing 11, the air blow-out port 13 is substantially closed by the upper plate 21. This state will be referred as "close state" of the louver 20. On the other hand, the state that the louver 20 is tilted with respected to the upper face of the housing 11 will be referred to as "open state".

Under the open state of the louver 20, air passing through the gas-liquid contact member 53 can be discharged from the air blow-out port 13. Here, the air discharged from the air blow-out port 13 is discharged along the upper plate 21 and the lower plate 22 of the louver 20. Therefore, by changing the tilt angle of the louver 20, the air discharging direction of the air filtering apparatus 1 can be adjusted. Furthermore, the louver 20 has a two-vane structure in which the upper plate 21 and the lower plate 22 are arranged in parallel to each other so as to be spaced from each other at a predetermined interval, so that the louver 20 has an action of rectifying the air blown out from the air blow-out port 13. Accordingly, there is an advantage that air can be smoothly discharged in conformity to the tilt angle of the louver 20.

Furthermore, if the louver 20 is set to the close state while the fan motor 32 is stopped, air in the housing 1 hardly leaks to the outside. Therefore, as described later, when active oxygen species of high concentration are generated in the electrolytic bath 46, odor inherent to these materials hardly leak to the outside. Accordingly, the active oxygen species of high concentration can be utilized with keeping comfortable the indoor environment under which the air filtering apparatus 1 is set.

Figure 7A:
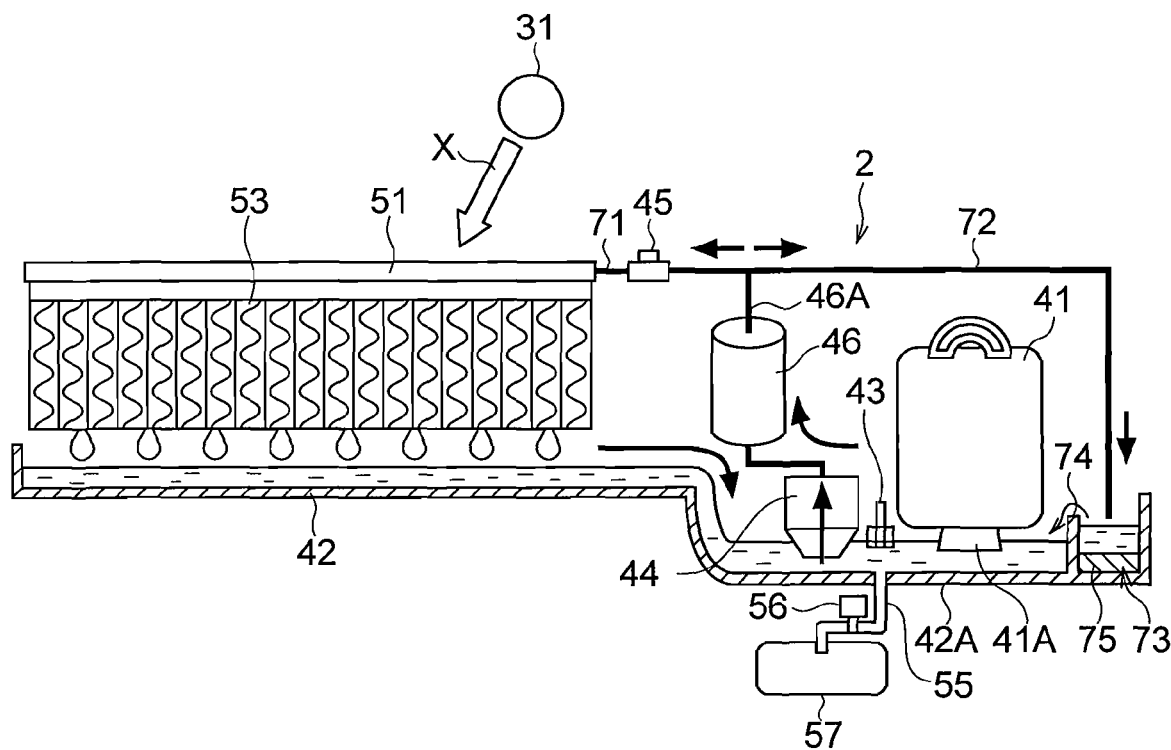
FIG. 7A is a diagram showing the construction of an electrolytic water circulating unit.
Figure 7B:
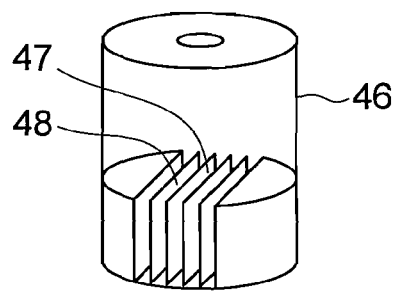
FIG. 7B is a diagram showing the construction of an electrolytic bath.

FIGS. 7A and 7B are diagrams showing the aspect of supplying electrolytic water, wherein FIG. 7A is a diagram showing the construction of the electrolytic water circulating unit 2, and FIG. 7B is a diagram showing the detailed construction of the electrolytic bath 46.

The supply of the electrolytic water to the gas-liquid contact member 53 will be described with reference to FIGS. 7A and 7B. In this embodiment, a case where tap water is filled in the water supply tank 41 and the air filtering apparatus 1 is operated will be described.

When the water supply tank 41 filled with tap water is set in the air filtering apparatus 1, the tap water is supplied form the water supply tank 41 to the water receiving tray 42 as described above, and the water level of the water receiving tray 42 reaches a predetermined level. Water in the water receiving tray 42 is pumped by the circulating pump 44, and supplied to the electrolytic bath 46. As shown in FIG. 7B, the electrolytic bath 46 is equipped with at least one pair of positive and negative electrodes 47 and 48, and by applying a voltage between the electrodes 47 and 48, tap water supplied to the electrolytic bath 46 is electrolyzed and electrolytic water containing active oxygen species is generated. Here, the active oxygen species is oxygen having higher oxidizing activity than normal oxygen and relevant materials thereto, and contain not only so-called narrowly-defined active oxygen such as superoxide anion, singlet oxygen, hydroxyl radical and hydrogen peroxide, but also so-called broadly-defined active oxygen such as ozone, hypochlorous acid, hypohalous acid, etc. The electrolytic bath 46 is disposed in proximity to the gas-liquid contact member 53, and thus the active oxygen species generated by electrolyzing tap water can be immediately supplied to the gas-liquid contact member 53.

The electrodes 47, 48 are constructed by two electrode plates each of which comprises a base of Ti (titan) and a coated layer of Ir (iridium), Pt (platinum). The current value flowing in the electrodes 47, 48 is set so that the current density is equal to several mA (milliampere)/cm$^2$ (square centimeter) to several tens MA/cm$^2$, and a predetermined free residual chlorine concentration (for example, 1 mg(milligram)/l (liter) occurs.

More specifically, by supplying current to tap water through the electrodes 47, 48, the following reaction occurs at the cathode:

$$4H^+ + 4e^- + (4OH^-) \rightarrow 2H_2 + (4OH^-)$$

Furthermore, the following reaction occurs at the anode:

$$2H_2O \rightarrow 4H^+ + O_2 + 4e^-$$

At the same time, chlorine ions contained water (chlorine ions are added in tap water in advance) reacts as follows:

$$2Cl^- \rightarrow Cl_2 + 2e^-$$

Furthermore, $Cl_2$ thus generated reacts with water as follows:

$$Cl_2 + H_2O \rightarrow HClO + HCl$$

That is, hypochlorous acid (HClO) and hydrogen chloride (HCl) occur.

In this construction, as described above, a part of the electrolytic water generated in the electrolytic bath 46 is returned to the water receiving tray 42 through the bypass pipe 72. Hypochlorous acid contained in the returned electrolytic water is hardly consumed. Therefore, when the electrolytic water returned through the bypass pipe 72 and the electrolytic water passing through the gas-liquid contact member 53 are mixed with each other in the water receiving tray, the concentration of hypochlorous acid in the electrolytic water in the water receiving tray is higher than that of the electrolytic water passing through the gas-liquid contact member 53. Accordingly, the water (electrolytic water) in the water receiving tray is fed to the electrolytic bath 46 and electrolyzed again, whereby electrolytic water containing a high concentration of hypochlorous acid can be prepared.

According to this construction, for example, even in the case of water in a district where the amount of chloride ion is small, electrolytic water containing hypochlorous acid whose concentration is so sufficient that virus, etc. to be filtered can be inactivated can be prepared. The adjustment of the concentration of hypochlorous acid (active oxygen species) in electrolytic water may be performed by adjusting the voltage applied between the electrodes 47 and 48 to adjust the current value flowing between the electrodes 47 and 48. Specifically, by changing the voltage applied between the electrodes 47, 48 to increase the current value, the concentration of hypochlorous acid in electrolytic water can be set to a high concentration.

The concentration of the active oxygen species in the electrolytic water is adjusted so that virus, etc. to be filtered are inactivated. The adjustment of the concentration of the active oxygen species is performed by adjusting the voltage applied between the electrodes 47, 48 to adjust the value of current to flow between the electrodes 47, 48. Specifically, by changing the voltage applied between the electrodes 47, 48 to increase the current value, the concentration of hypochlorous acid in the electrolytic water can be increased.

Hypochlorous acid occurring at the anode is contained in the broadly-defined active oxygen species and has strong oxidizing action and a bleaching action. Water solution in which hypochlorous acid is dissolved, that is, electrolytic water generated in the air filtering apparatus 1 exercises various kinds of air cleaning effects such as inactivation of virus, etc., sterilization, decomposition of organic compounds, etc. When electrolytic water containing hypochlorous acid is dropped from the water spray box 51 to the gas-liquid contact member 53, air blown out from the air blowing fan 31 is brought into contact with hypochlorous acid in the gas-liquid contact member 53. Accordingly, virus, etc. floating in the air are inactivated, and also odor materials contained in the air concerned react with hypochlorous acid to be decomposed or ionized, so that the order materials are dissolved in the water. Accordingly, air filtering and deodorization are performed, and cleaned air is discharged from the gas-liquid contact member 53.

An inactivating mechanism of virus, etc. by the active oxygen species will be described by exemplifying influenza virus. The active oxygen species functions to break down and vanish (remove) the surface protein (spike) of the virus concerned which is indispensable for infection. When the surface protein of influenza virus is broken down, the influenza virus is not joined to a receptor which is necessary for infection of the virus concerned, so that infection can be prevented. Therefore, influenza virus floating in the air is brought into contact with the electrolytic water containing the active oxygen species in the gas-liquid contact member 53, so that the influenza virus loses so-called infection power, and thus the infection can be prevented.

Accordingly, even when the air filtering apparatus 1 is set in a so-called large space such as a kindergarten, an elementary/junior high/high school, long-term care insurance facilities, a hospital or the like, air cleaned (sterilized, inactivated, deodorized, etc.) by electrolytic water is enabled to broadly go around in a large space. Therefore, air filtering and deodorization in a large space can be efficiently performed.

Furthermore, the electrolytic water dropped from the water spray box 51 to the gas-liquid contact member 53 moves downwardly along the gas-liquid contact member 53, and finally falls to the water receiving tray 42. The electrolytic water falling to the water receiving tray 42 is pumped by the circulating pump 44 again and supplied through the electrolytic bath 46 to the gas-liquid contact member 53. As described above, according to the construction of this embodiment, the water is supplied in a circulating style, and air can be efficiently filtered for a long time by using a small amount of water effectively. Furthermore, when the amount of water circulated in the electrolytic water circulating unit 2 is reduced due to vaporization or the like, a proper amount of water in the water supply tank 41 is supplied to the water receiving tray 41.

In the air filtering apparatus 1 of this embodiment, water stocked in the water receiving tray 42 can be properly discharged. Specifically, as shown in FIGS. 2 to 7, a tank-like drain receiver 57 which has a predetermined width and is equipped with an opening at the upper portion thereof is disposed below the water stock portion 42A. The drain receiver 57 is mounted on the support plate 37 (FIG. 2), and it can be inserted and taken out into/from the drain receiver take-out port 15 of the housing 11 (FIG. 1). The drain pipe 55 is joined to the stock portion 42A of the water receiving tray 42, and a drain valve 56 for opening/closing the drain pipe 55 is provided to the drain pipe 55. The tip of the drain pipe 55 extends downwardly, and intrudes from the opening of the drain receiver 57 into the drain receiver 57.

The bottom surface of the stock portion 42A is opened at the joint portion to the drain pipe 55 so that water in the stock portion 42A flows out from the open portion, and the drain pipe 55 extends downwardly from the stock portion 42A. Therefore, the drain valve 56 is opened under the control of the controller 60 (FIG. 8), and the water in the water receiving tray 42 passes through the drain pipe 55 and flows to the drain receiver 57. As described above, the drain pipe 55 provided to the water receiving tray is used, and the opening/closing of the drain valve 56 is controlled, whereby water in the air filtering mechanism 10 can be withdrawn/discharged by the drain receiver 57. Furthermore, the drain receiver 57 is provided with a grip portion 57A which can be easily grasped, and thus it can be easily inserted and taken out into/from the drain receiver take-out port 15 (FIG. 1).

FIG. 8 is a functional block diagram showing the construction of the control system of the air filtering apparatus 1.

As shown in FIG. 8, in the air filtering apparatus 1, the fan motor 32, the circulating pump 44, the opening/closing valve 45, the drain valve 56, the louver driving motor 68 for opening/closing the louver 20 and the power supply portion 67 for supplying power to the respective parts are connected to the controller 60, and operated according to the control of the controller 60.

Furthermore, various kinds of switches, indicator lamps, etc. disposed on the operation panel 16 are connected to the controller 60, and also the water receiving tray float switch 43, the electrodes 47, 48, and the electrolytic bath float switch 66 for detecting the water level in the electrolytic bath 46 are connected to the controller 60.

The controller 60 includes a microcomputer 61 for controlling the whole of the air filtering apparatus 1, a storage unit 62 for storing control programs executed by the microcomputer 61 and data such as control parameters, etc., a timer counter 63 for carrying out a time counting operation on the basis of the control of the microcomputer 61, an input unit 64 for detecting an operation of the operation panel 16 and outputting the operation content to the microcomputer 61, and an output unit 65 for outputting the processing result of the microcomputer 61 by controlling turn-on of the indicator lamps (not shown) of the operation panel 16 or the like.

The microcomputer 61 reads in and executes the control programs stored in the storage unit 62 in advance, and also reads in the control parameters stored in the storage unit 62 to operate the respective parts of the air filtering apparatus 1.

Specifically, when the operation of instructing start of the operation is carried out on the operation panel 16 and the information representing this operation is input from the input unit 64, the microcomputer 61 operates the circulating pump 44 to start the circulation of water, and also applies a voltage between the electrodes 47, 48 to generate electrolytic water. Furthermore, the microcomputer 61 operates the louver driving motor 68 to set the louver 20 to an open state. Thereafter, the microcomputer 61 starts to operate the fan motor 32, thereby starting the air blowing operation of the air blowing fan 31. Through the series of operations described above, the air filtering operation of the air filtering apparatus 1 is started.

Furthermore, in connection with the start of the air filtering operation, the microcomputer 61 controls the time counter 63 to start the counting operation of the operation time. The timer counter 63 can accumulatively count the operation time. Accordingly, even after the air filtering apparatus 1 stops the air filtering operation, the timer counter 63 can continue to count the operation time without resetting the count value when the air filtering operation is resumed.

During execution of the air filtering operation, the microcomputer 61 measures the voltage applied between the electrodes 47 and 48 and the current value flowing between the electrodes 47 and 48. Then, the microcomputer 61 monitors the electrical conductivity calculated from the voltage value and the current value, judges the concentration of the electrolytic water (the concentration of the active oxygen species) in the electrolytic bath 46 on the basis of the electrical conductivity, and properly adjusts the voltage to be applied between the electrodes 47 and 48. In this construction, the microcomputer 61 and the electrodes 47 and 48 function as a current value detecting unit for detecting the current value flowing between the electrodes 47, 48. Furthermore, during execution of the air filtering operation of the air filtering apparatus 1, when it is detected by the electrolytic bath float switch 66 that the water level in the electrolytic bath 46 is lower than the predetermined water level and also when it is detected by the water receiving tray float switch 43 that the water level of the water receiving tray 42 is lower than the predetermined water level, the microcomputer 61 stops application of the voltage between the electrodes 47 and 48, stops the operation of the circulating pump 44 and the fan motor 32, and also makes the output portion 65 display an alarm.

Furthermore, when the operation of instructing the stop of the operation is carried out on the operation panel 16 and the information representing this operation is input from the input unit 64, the microcomputer 61 stops application of the voltage between the electrodes 47, 48 and also stops the circulating pump 44. Still furthermore, the microcomputer 61 stops the fan motor 32 and the air blowing operation of the air blowing fan 31, and then operates the louver driving motor 68 to set the louver 20 to a close state. Through the series of operations described above, the air filtering operation of the air filtering apparatus 1 is stopped. At the time when the air filtering operation is stopped, the microcomputer 61 controls the output unit 65 to stop the display indicating that the air filtering apparatus 1 is under operation, and also controls the timer counter 63 to stop the time counting operation.

Next, the operation of inverting the polarities of the electrodes 47 and 48 to remove scale deposited on the surfaces of the electrodes will be described.

FIG. 9 is a flowchart showing the operation of discharging to the filter unit the scale which is exfoliated (removed) from the electrodes by inverting the polarities of the electrodes 47, 48. In this construction, the microcomputer 61 functions as a scale removing unit for removing scale deposited on the surface of the electrode by inverting the polarities of the electrodes.

The microcomputer 61 judges whether the operation time of the air filtering operation measured by the timer counter 63 has passed by a predetermined time (for example, 30 minutes) from the previous polarity inversion time of the electrodes (step S1). If it is judged in step S1 that the operation time has elapsed from the previous polarity inversion time by the predetermined time (step S1; Yes), the microcomputer 61 inverts the polarities of the electrodes 47, 48 (step S2). In general, when electrolysis is conducted, scale (for example, calcium-based scale such as calcium carbonate, magnesium-based scale such as magnesium carbonate) derived from inorganic materials contained in water introduced to the electrolytic bath 46 is particularly deposited on the electrode at the cathode. When the scale is deposited on the electrode, the electrical conductivity is lowered, and it is difficult to continually carry out electrolysis, so that the electrolysis performance is lowered. On the other hand, if the polarities of the electrodes are inverted, the cathode and the anode are replaced by each other, and thus the scale deposited on the surface of the electrode is exfoliated.

Subsequently, the microcomputer 61 closes the opening/closing valve 45 (step S3). Accordingly, the scale exfoliated from the cathode electrode is returned to the water receiving tray 42 through the bypass pipe 72 together with electrolytic water flowing out from the electrolytic bath 46. As described above, the filter unit 73 is formed in the water receiving tray 42, and the scale contained in the electrolytic water is collected and removed by the filter member 75 of the filter unit 73. Accordingly, only the electrolytic water from which the scale is removed flows over the dam 74 of the filter unit 73 and flows into the stock portion 42A of the water receiver.

Subsequently, when the opening/closing valve 45 is closed, the microcomputer 61 increases the voltage value applied between the electrodes 47, 48 so that the voltage value concerned is higher than that under the normal air filtering operation (step S4) (step S4). Accordingly, the scale deposited on the cathode can be more early exfoliated.

Furthermore, the microcomputer 61 sets the rotational number of the circulating pump to a higher value than that under the normal air filtering apparatus (step S5). Accordingly, the flow rate of the water stream passing through the electrolytic path is increased, and thus the scale exfoliated from the cathode can be early discharged from the electrolytic bath 46 with riding on this water stream.

Subsequently, the microcomputer 61 judges whether scale is exfoliated from the surface of the electrode (step S6). Specifically, the microcomputer 61 monitors the current value flowing between the electrodes 47, 48, and judges whether this current value is equal to a predetermined threshold value or more. When scale is deposited on the surface of the electrode, the scale serves as a resistor, so that the current value flowing between the electrodes 47, 48 is reduced. On the other hand, the polarities of the electrodes are inverted in step S2, and thus the scale deposited on the surface of the electrode is exfoliated, and the current value flowing between the electrodes 47, 48 is increased in connection with the exfoliation of the scale. If it is judged in step S6 that the current value flowing between the electrodes 47, 48 is equal to the predetermined value or more (step S6; Yes), it is judged that the scale is exfoliated from the electrode, and thus the processing shifts to step S7.

Subsequently, the microcomputer 61 measures the time from the time point when the current value is equal to the predetermined threshold value or more, and judges whether this time passes over a predetermined time (for example, 10 seconds) (step S7). This predetermined time is set to such a sufficient value that the scale exfoliated from the electrode is discharged from the electrolytic bath 46. Accordingly, in this judgment, if it is judged that the time has passed over the predetermined time, it is judged that the scale exfoliated from the electrode is discharged from the electrolytic bath 46. Therefore, the opening/closing valve 45 is opened (step S8), the voltage value applied between the electrodes and the rotational frequency of the circulating pump are returned to those values under the normal air filtering operation (step S9), and the processing is finished.

According to this embodiment, the water in the electrolytic bath 46 is electrolyzed by applying the voltage between the electrodes 47, 48 in the electrolytic bath 46 to generate electrolytic water, the generated electrolytic water is supplied to the gas-liquid contact member 53, and air is fed to the gas-liquid contact member 53, whereby the air is filtered. Furthermore, the microcomputer 61 inverts the polarities of the electrodes every predetermined time to remove scale deposited on the electrode. Therefore, the labor for maintenance of the electrodes can be reduced, and the maintenance frequency can be reduced. Accordingly, even when the air filtering apparatus is operated for a long term, the electrolysis performance and the durability can be maintained even when the air filtering apparatus is operated for a long term, and further the air filtering performance can be maintained. Furthermore, the microcomputer 61 judges on the basis of the current value flowing between the electrodes 47, 48 whether scale is removed from the electrode surface. Therefore, the scale can be surely removed from the electrodes 47, 48, and the air filtering can be efficiently executed by shifting to the air filtering operation immediately after the scale is removed, for example.

Furthermore, according to this embodiment, when the detected current value is above the predetermined threshold value, the microcomputer 61 judges that scale is removed from the electrode surface. Therefore, the removal or non-removable of scale can be judged with a simple construction of monitoring the current value flowing between the electrodes.

Still furthermore, according to this embodiment, the air filtering apparatus is further equipped with the bypass pipe 72 through which the electrolytic water flowing out from the electrolytic bath 46 bypasses the gas-liquid contact member 53, and the opening/closing valve 45 for prohibiting electrolytic water containing scale from being supplied to the gas-liquid contact member 53 when the polarities of the electrodes 47, 48 are inverted and also guiding the electrolytic water concerned to the bypass pipe 72. Therefore, the gas-liquid contact member 53 can be prevented from being clogged with scale, and the labor for the maintenance of the gas-liquid contact member 53 can be reduced.

Still furthermore, according to this embodiment, when it is judged that scale is removed from the electrode surface, the microcomputer 61 controls the opening/closing valve 45 to allow supply of electrolytic water to the gas-liquid contact member 53, and thus electrolytic water from which scale is removed is immediately supplied to the gas-liquid contact, so that the air filtering can be efficiently executed.

According to this embodiment, the bypass pipe 72 is provided with the filter unit 73 for collecting scale. Therefore, the scale can be removed from electrolytic water by the filter unit 73. Accordingly, even when the electrolytic water is circulated, the scale can be prevented from being supplied to the gas-liquid contact member 53 and thus inducing clogging in the gas-liquid contact member 53.

Furthermore, the filter unit 73 is disposed in the water receiving tray 42 for receiving water passing through the gas-liquid contact member 53, and thus the exchange timing of the filter unit 75 disposed in the filter unit 73 can be simply judged through visual check. Furthermore, when the filter unit 75 is exchanged, the filter unit 75 may be detached and exchanged by hands, so that the maintenance can be simply performed without using any tool.

The air filtering apparatus 1 of this embodiment is an example, and various modifications may be made without departing from the subject of the present invention.

For example, ozone ($O_3$) or hydrogen peroxide ($H_2O_2$) may be generated as active oxygen species. In this case, when platinum tantalum electrodes are used as the electrodes 47, 48, active oxygen species can be highly efficiently and stably generated from water in which ion species are rare.

At this time, at the anode, the following reaction occurs:

$2H_2O \rightarrow 4H^+ + O_2 + 4e^-$

Simultaneously with the above reaction, the following reactions occur, and ozone ($O_3$) is generated.

$3H_2O \rightarrow O_3 + 6H^+ + 6e^-$ $2H_2O \rightarrow O_3 + 4H^+ + 4e^-$

Furthermore, at the cathode, the following reactions occur:

$4H^+ + 4e^- + (4OH^-) \rightarrow 2H_2 + (4OH^-)$ $O_2^- + e^- + 2H^+ \rightarrow H_2O_2$ That is, $O_2^-$ generated through the electrode reaction and $H^+$ in solution are bonded to each other to generate hydrogen peroxide ($H_2O_2$).

Furthermore, in the above embodiment, tap water is supplied from the water supply tank 41. Tap water is added with chlorine compound for the purpose of sterilization, and thus it contains chloride ions. Hypochlorous acid and hydrochloric acid are generated through the reaction of chloride ions. This is not limited to the case where tap water is used. Active oxygen species containing halogen can be generated through the same reaction insofar as water contains halide ions by adding or mixing halide to water supplied to the electrolytic bath 46.

According to this embodiment, the opening/closing valve 45 is provided to only the water feed pipe 71. However, an opening/closing valve may be also provided to the bypass pipe 72, and the opening/closing operation of any opening/closing valve may be controlled. Furthermore, a three-way valve may be provided at the branch portion between the water feed pipe 71 and the bypass pipe 72 to supply electrolytic water to any one of the water feed pipe 71 and the bypass pipe 72.

Furthermore, in this embodiment, the discharge port 46A is provided on the upper surface of the electrolytic bath 46. however, the discharge port may be provided to the lower surface of the electrolytic bath in consideration of the fact that the specific gravity of scale is larger than that of water.

Still furthermore, in the air filtering apparatus 1, the same reaction can be induced even when water containing rare ion species (containing pure water, purified water, well water, some kinds of tap water, etc.) is used. That is, by adding halide (salt or the like) to water containing rare ion species, the same reaction is induced and active oxygen species can be achieved. Furthermore, the above embodiment adopts a water supply system based on the water supply tank 41 which can be freely inserted and taken out. However, in place of use of the water supply tank 41, a water pipe-distributing and supplying system in which a tap water pipe is connected to directly supply city water to the air filtering apparatus 1 may be used.

What is claimed is:

1. An air filtering apparatus for electrolyzing water in an electrolytic bath by applying a voltage between electrodes in the electrolytic bath, supplying the generated electrolytic water to a gas-liquid contact member and blowing air to the gas-liquid contact member to filter the air, comprising:
a scale removing unit for inverting the polarities of the electrodes to remove scale deposited on the electrodes;
a judging unit for judging on the basis of a current value flowing between the electrodes whether the scale is removed from the surface of the electrode;
a bypass passage through which electrolytic water flowing out from the electrolytic bath bypasses the gas-liquid contact member;
a bypass valve for prohibiting the electrolytic water containing the scale from being supplied to the gas-liquid contact member and guiding the electrolytic water to the bypass passage; and
a controller being operative to close the bypass valve when the polarities of the electrodes are inverted, and to open the bypass valve in response to the judging unit judges that the scale is removed from the surface of the electrode.

2. The air filtering apparatus according to claim 1, wherein when it is judged that the scale has been removed from the electrode surface, the bypass valve is controlled to allow supply of the electrolytic water to the gas-liquid contact member.

3. The air filtering apparatus according to claim 1, wherein the bypass passage is equipped with a filter unit for collecting the scale.

4. The air filtering apparatus according to claim 3, wherein the filter unit is disposed in a water receiving tray for receiving water passing through the gas-liquid contact member.

5. The air filtering apparatus according to claim 1, wherein the controller is operative to open the bypass valve in accordance with the controller judges a predetermined time is passed after the judging unit judges that the scale is removed from the surface of the electrode.

* * * * *